(12) United States Patent
Kubota et al.

(10) Patent No.: US 10,073,015 B2
(45) Date of Patent: Sep. 11, 2018

(54) SAMPLE SMEAR APPARATUS AND SAMPLE SMEAR METHOD

(71) Applicant: SYSMEX CORPORATION, Kobe-shi, Hyogo (JP)

(72) Inventors: Shogo Kubota, Kobe (JP); Mitsuo Yamasaki, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/498,862

(22) Filed: Apr. 27, 2017

(65) Prior Publication Data

US 2017/0315030 A1    Nov. 2, 2017

(30) Foreign Application Priority Data

Apr. 28, 2016   (JP) .................. 2016-092068

(51) Int. Cl.

| | |
|---|---|
| *G01N 1/00* | (2006.01) |
| *G01N 1/28* | (2006.01) |
| *G02B 21/34* | (2006.01) |
| *G01N 35/00* | (2006.01) |
| *G01N 35/04* | (2006.01) |

(52) U.S. Cl.
CPC ..... *G01N 1/2813* (2013.01); *G01N 35/00029* (2013.01); *G01N 35/04* (2013.01); *G02B 21/34* (2013.01); *G01N 2035/00039* (2013.01); *G01N 2035/00138* (2013.01)

(58) Field of Classification Search
CPC ....................................... G01N 1/00
See application file for complete search history.

(56) References Cited

U.S. PATENT DOCUMENTS

| | | | | |
|---|---|---|---|---|
| 5,854,075 | A | * | 12/1998 | Levine ............... G01N 1/2813 118/100 |
| 2005/0186114 | A1 | * | 8/2005 | Reinhardt ............... B01L 9/52 422/65 |
| 2006/0051241 | A1 | | 3/2006 | Higuchi et al. |
| 2013/0020175 | A1 | | 1/2013 | McKeen et al. |

FOREIGN PATENT DOCUMENTS

| | | |
|---|---|---|
| CN | 203877403 U | 10/2014 |
| CN | 203877556 U | 10/2014 |
| JP | 2000-074803 A | 3/2000 |
| JP | 2005-308566 A | 11/2005 |
| JP | 2005-315754 A | 11/2005 |
| JP | 2005-345229 A | 12/2005 |
| JP | 2009-145261 A | 7/2009 |
| WO | 2015/165019 A1 | 11/2015 |

\* cited by examiner

*Primary Examiner* — Jyoti Nagpaul
(74) *Attorney, Agent, or Firm* — Metrolexis Law Grouup, PLLC

(57) ABSTRACT

A sample smear apparatus of an embodiment includes: a slide feeder that feeds a slide glass before processing; a smear processor that smears a sample on the slide glass; and a slide transporter including a slide holder mechanism with an upper surface where to hold the slide glass and a transfer mechanism that moves the slide holder mechanism in a vertical direction and in a horizontal direction, the slide transporter arranged movably to the slide feeder and the smear processor.

17 Claims, 10 Drawing Sheets

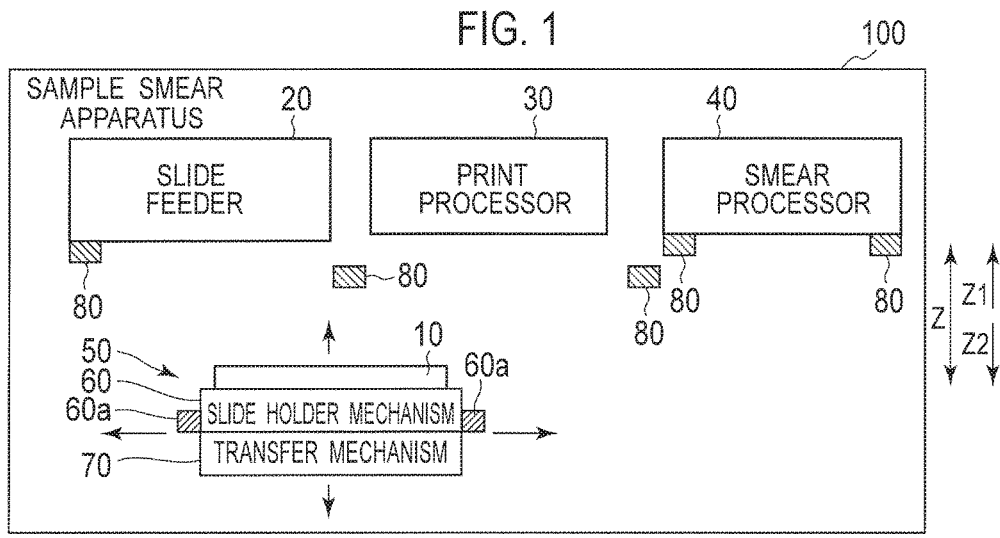
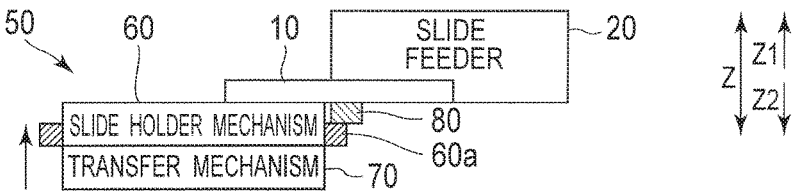
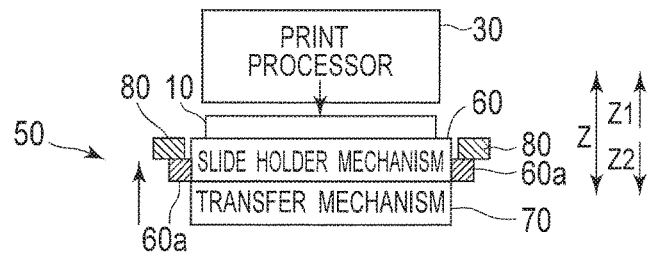
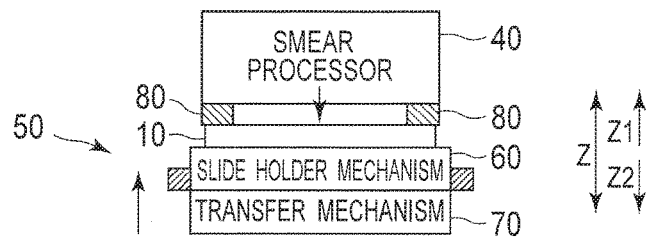

SAMPLE SMEAR APPARATUS AND SAMPLE SMEAR METHOD

CROSS REFERENCE TO RELATED APPLICATIONS

This application claims priority based on 35 USC 119 from prior Japanese Patent Application No. 2016-092068 filed on Apr. 28, 2016, entitled "SAMPLE SMEAR APPARATUS AND SAMPLE SMEAR METHOD", the entire contents of which are incorporated herein by reference.

BACKGROUND

The disclosure relates to a sample smear apparatus and a sample smear method.

A sample smear apparatus includes, as main constituent components: various processors such as a slide feeder which feeds a slide glass, a smear unit which smears a sample on the slide glass, a drier which dries the sample on the slide glass, and a printer which makes print on the slide glass; and a transporter which transports the slide glass. The slide glass is a plate having a thickness of about 1 mm, and processing of smearing and printing on the slide glass requires precise positioning.

In Japanese Patent Application Publication No. 2005-345229 (Patent Literature 1), a smear unit positions a slide glass in a vertical direction by lifting a support member that supports the slide glass from the lower surface side and bringing the upper surface of the slide glass into contact with a fixed plate for positioning.

As described above, in the conventional sample smear apparatus, each of the slider feeder and the processors is equipped with a mechanism for moving the slide glass up and down, such as a slide glass elevator mechanism provided in the smear unit. Therefore, the structures of the slide feeder and the processors are complicated.

SUMMARY

A sample smear apparatus according to a first aspect of the invention includes: a slide feeder which feeds a slide glass before processing; a smear processor which smears a sample on the slide glass; and a slide transporter which includes a slide holder mechanism with an upper surface where to hold the slide glass and a transfer mechanism which moves the slide holder mechanism in a vertical direction and in a horizontal direction, the slide transporter being movable to the slide feeder and the smear processor.

A sample smear method according to a second aspect of the invention is a sample smear method using a sample smear apparatus which feeds a slide glass before processing to a slide glass feed position and performs smear processing of the sample on the slide glass, the sample smear method including: moving a slide holder mechanism to the slide glass feed position; positioning the slide holder mechanism in a vertical direction by lifting the slide holder mechanism; feeding the slide glass to the positioned slide holder mechanism; moving the slide holder mechanism to a processing position for the smear processing after feeding the slide glass; positioning the slide glass in the vertical direction by lifting the slide holder mechanism; and performing the smear processing on the positioned slide glass.

BRIEF DESCRIPTION OF DRAWINGS

FIG. 1 is a schematic view illustrating an overview of a sample smear apparatus according to one or more embodiments.

FIGS. 2A, 2B and 2C are schematic views for explaining positioning a slide glass on slide holder mechanism in a vertical direction.

DETAILED DESCRIPTION

Figure 3:
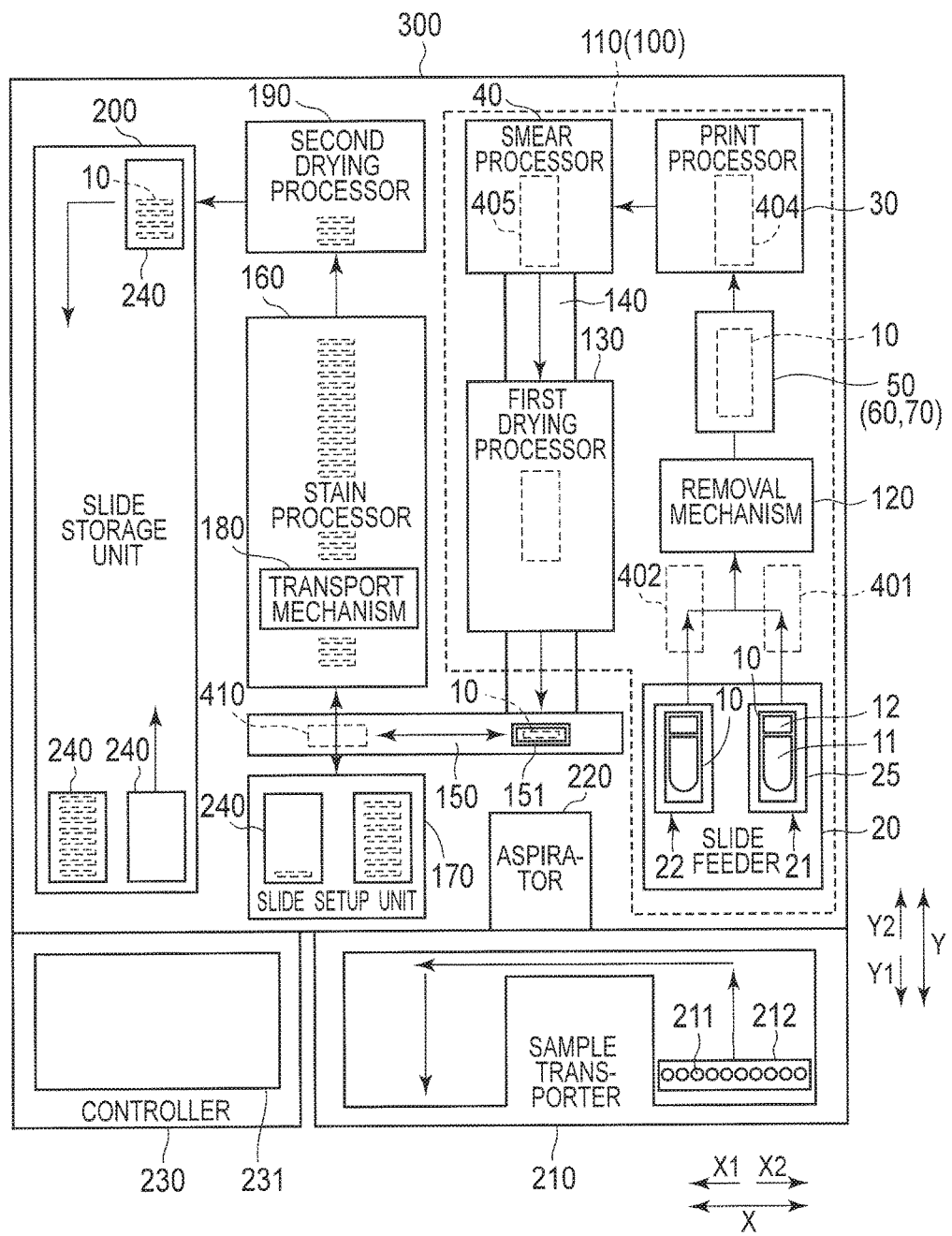
FIG. 3 is a plan view for explaining an example of an overall configuration of a smear preparation apparatus.

Embodiments are explained with reference to drawings. In the respective drawings referenced herein, the same constituents are designated by the same reference numerals and duplicate explanation concerning the same constituents is basically omitted. All of the drawings are provided to illustrate the respective examples only. No dimensional proportions in the drawings shall impose a restriction on one or more embodiments. For this reason, specific dimensions and the like should be interpreted with the following descriptions taken into consideration. In addition, the drawings may include parts whose dimensional relationship and ratios are different from one drawing to another.

[Overview of Sample Smear Apparatus]

With reference to FIG. 1, description is given of an overview of sample smear apparatus 100 according to one or more embodiments.

Sample smear apparatus 100 is an apparatus for smearing a sample on slide glass 10. The sample is a biological specimen collected from a sample under test (subject), for example, blood, urine, cells, and the like.

As illustrated in FIG. 1, sample smear apparatus 100 includes slide feeder 20, smear processor 40, and slide transporter 50.

Slide glass 10 is a rectangular plate-like member, for example. Slide glass 10 has, for example, a smear region for smearing the sample and a print region for displaying various kinds of information such as sample information, on its surface. The smear region is formed in a predetermined range extending in a longitudinal direction in the center of slide glass 10 in the longitudinal direction, for example. The print region is formed away from the smear region at one end of slide glass 10 in the longitudinal direction. The print region is a part that is processed to be printable by coating slide glass 10 with a resin material or the like, for example. In the print region, a sample number, a date, a bar code or two-dimensional code, and the like can be printed.

Slide feeder 20 feeds slide glasses 10 before processing. Slide feeder 20 can house more than one slide glass 10. Slide feeder 20 passes slide glass 10 to slide transporter 50. In sample smear apparatus 100, slide glass 10 fed from slide feeder 20 is transported to print processor 30 and smear processor 40.

Sample smear apparatus 100 may include print processor 30. In the configuration example of FIG. 1, sample smear apparatus 100 includes print processor 30. Print processor 30 performs printing on slide glass 10. Print processing by print processor 30 is processing of printing various kinds of information such as sample information in the print region on the surface of slide glass 10. Print processor 30 uses a heretofore known printer such as a thermal-transfer printer and an ink-jet printer, for example, to perform the print processing.

Smear processor 40 has smears the sample on slide glass 10. Smear processing by smear processor 40 is processing of smearing the sample in the smear region on the surface of slide glass 10. The sample is smeared in an amount and an application thickness suitable for microscopical examination using slide glass 10. For the smear processing, a smear method (so-called wedge method) using a smear member such as a drawing glass, or other smear methods can be adopted. Smear processor 40 performs the smear processing by using a smear mechanism corresponding to the smear method to be adopted.

Slide transporter 50 is configured to be movable to slide feeder 20 and smear processor 40. Slide transporter 50 includes: slide holder mechanism 60 with an upper surface for holding slide glass 10; and transfer mechanism 70 which moves slide holder mechanism 60 in a vertical direction and in a horizontal direction.

Slide transporter 50 can use transfer mechanism 70 to position slide holder mechanism 60 at slide feeder 20 and smear processor 40.

In the configuration of sample smear apparatus 100 further including print processor 30, slide transporter 50 may be configured to be movable to slide feeder 20, print processor 30, and smear processor 40. Slide transporter 50 may also be movable to slide feeder 20 and smear processor 40, and not to print processor 30. In such a case, a transporter provided separately from slide transporter 50 may transport slide glass 10 to print processor 30, for example. Slide transporter 50 may further transport slide glass 10 to parts other than slide feeder 20, print processor 30, and smear processor 40.

When positioning slide holder mechanism 60 at slide feeder 20, slide transporter 50 receives slide glass 10 before smearing from slide feeder 20 onto slide holder mechanism 60. When positioning slide holder mechanism 60 at print processor 30, slide transporter 50 transports slide glass 10 held on slide holder mechanism 60 to a predetermined processing position at print processor 30. When positioning slide holder mechanism 60 at smear processor 40, slide transporter 50 transports slide glass 10 held on slide holder mechanism 60 to a predetermined processing position at smear processor 40.

Slide holder mechanism 60 holds slide glass 10 on its upper surface in a flat placement state where a smear surface of slide glass 10 faces upward, for example. Thus, print processor 30 and smear processor 40, for example, can perform print processing and smear processing on slide glass 10 held on the upper surface of slide holder mechanism 60 without handing over the slide glass to another holding mechanism.

Transfer mechanism 70 is an orthogonal triaxial transfer mechanism for moving slide holder mechanism 60 in the vertical and horizontal directions, for example. Transfer mechanism 70 may also be a biaxial transfer mechanism with one vertical axis and one horizontal axis. Transfer mechanism 70 includes a combination of direct operated mechanisms, which perform linear movement, for example. The direct operated mechanisms may be, for example, a belt-pulley mechanism, a rack and pinion mechanism, a linear motor mechanism, an actuator such as an air cylinder and a solenoid, and the like.

Here, sample smear apparatus 100 may also include vertical positioning members 80. In more than one of slide feeder 20, print processor 30, and smear processor 40, vertical positioning members 80 are configured to position slide holder mechanism 60 or slide glass 10 in a vertical direction by coming into contact with predetermined portions of slide holder mechanism 60 or slide glass 10 lifted by transfer mechanism 70 in slide transporter 50. In the configuration example of FIG. 1, sample smear apparatus 100 includes vertical positioning members 80. Alternatively, sample smear apparatus 100 may include no vertical positioning members 80.

Vertical positioning members 80 are provided in more than one of slide feeder 20, print processor 30, and smear processor 40, for example. FIG. 1 illustrates a configuration example where vertical positioning members 80 are provided in all of slide feeder 20, print processor 30, and smear processor 40. In a configuration in which slide transporter 50 transports slide glass 10 to only some of slide feeder 20, print processor 30, and smear processor 40, vertical positioning members 80 may be provided in portions of slide feeder 20, print processor 30, and smear processor 40, to which slide transporter 50 can be moved.

FIGS. 2A, 2B, and 2C illustrate configuration examples of vertical positioning members 80 in each of slide feeder 20, print processor 30, and smear processor 40. As illustrated in FIG. 2A, vertical positioning member 80 is provided in slide feeder 20, for example. In the configuration example FIG. 2B, vertical positioning member 80 is provided to come into contact with predetermined portion 60a of slide holder mechanism 60, which is lifted from below, in the vertical direction (Z-direction) in slide feeder 20. Slide glass 10 on the upper surface of slide holder mechanism 60 is positioned at a predetermined feed height position by vertical positioning member 80 coming into contact with predetermined portion 60a. Thus, slide glass 10 is passed to slide holder mechanism 60 from slide feeder 20 at the feed height position thus set.

As illustrated in FIG. 2B, vertical positioning members 80 are provided in print processor 30, for example. In the configuration example FIG. 2B, vertical positioning members 80 are provided to come into contact with predetermined portions 60a of slide holder mechanism 60, which is lifted from below, in the vertical direction (Z-direction) in print processor 30. Slide glass 10 on the upper surface of slide holder mechanism 60 is positioned at a predetermined print height position by vertical positioning members 80 coming into contact with predetermined portions 60a. Thus, slide glass 10 on slide holder mechanism 60 is printed by print processor 30 at the print height position thus set.

As illustrated in FIG. 2C, vertical positioning members 80 are provided in smear processor 40, for example. In the configuration example of FIG. 2C, vertical positioning members 80 are provided to come into contact with slide glass 10 on slide holder mechanism 60, which is lifted from below, in the vertical direction (Z-direction) in smear processor 40. Slide glass 10 on the upper surface of slide holder mechanism 60 is positioned at a predetermined smear height position by vertical positioning members 80 coming into contact with slide glass 10. Thus, slide glass 10 on slide holder mechanism 60 is printed by smear processor 40 at the smear height position thus set.

Next, description is given of a sample smear method using the sample smear apparatus with the above configuration. Sample smear apparatus 100 moves slide holder mechanism 60 to a feed position of slide glass 10. Sample smear apparatus 100 performs vertical positioning of slide holder mechanism 60 by lifting slide holder mechanism 60. Sample smear apparatus 100 feeds slide glass 10 to slide holder mechanism 60 thus positioned.

After feeding slide glass 10, sample smear apparatus 100 moves slide holder mechanism 60 to a processing position for smear processing. Sample smear apparatus 100 performs vertical positioning of slide glass 10 by lifting slide holder mechanism 60. Sample smear apparatus 100 performs smear processing on slide glass 10 thus positioned.

Note that, in the case of performing feeding, print processing, and smear processing, the print processing is performed as in the above case. Specifically, slide holder mechanism 60 is moved to a processing position for the print processing, and then vertical positioning of slide holder mechanism 60 or slide glass 10 is performed. Thereafter, the print processing is performed on slide holder mechanism 60 or slide glass 10 thus positioned. In this case, the print processing may be performed either before or after the smear processing.

With the above configuration, vertical positioning of slide glass 10 can be performed by transfer mechanism 70 lifting slide holder mechanism 60 in slide transporter 50. In such a configuration of slide transporter 50 transporting slide glass 10 while moving to more than one location, an elevator mechanism for the vertical positioning can be shared at more than one location by providing transfer mechanism 70 capable of vertical movement on slide transporter 50 side. Therefore, the structures of slide feeder 20 and smear processor 40 can be simplified compared with a case where elevator mechanisms are individually provided in slide feeder 20 and the respective processors. As a result, the structures of slide feeder 20 and the processors can be simplified in sample smear apparatus 100.

Moreover, when sample smear apparatus 100 is provided with print processor 30, common slide transporter 50 can transport slide glass 10 between slide feeder 20, print processor 30, and smear processor 40. Thus, the apparatus configuration can be simplified. Furthermore, when sample smear apparatus 100 is provided with vertical positioning members 80, a simple configuration in which predetermined portions 60a of slide holder mechanism 60 or a slide glass come(s) into contact with vertical positioning members 80 can be adopted, which enables easy accuracy control for the positioning of slide glass 10.

[Configuration Example of Smear Preparation Apparatus]

With reference to FIG. 3, description is given below of a configuration example of smear preparation apparatus 300, in which sample smear apparatus 100 illustrated in FIG. 1 is applied to a sample smear unit in smear preparation apparatus 300. Smear preparation apparatus 300 is an apparatus for performing smear processing of smearing a sample on slide glass 10 and also performing sample stain processing on slide glass 10 with the sample smeared thereon. The sample is blood, for example.

(Overall Configuration)

Sample smear apparatus 100 including slide feeder 20, print processor 30, smear processor 40, slide transporter 50, and vertical positioning members 80 illustrated in FIG. 1 is provided as smear unit 110 in smear preparation apparatus 300 in the configuration example of FIG. 3. In the configuration example of FIG. 3, smear unit 110 further includes removal mechanism 120, first drying processor 130, and discharge mechanism 140. Also, in the configuration example of FIG. 3, smear preparation apparatus 300 includes transport mechanism 150, stain processor 160, slide setup unit 170, transport mechanism 180, second drying processor 190, and slide storage unit 200. In the configuration example of FIG. 3, smear preparation apparatus 300 further includes sample transporter 210, aspirator 220, and controller 230.

In the following description, it is assumed that two directions orthogonal to each other within a plane parallel to an installation surface of smear preparation apparatus 300 (that is, within a horizontal plane) are X-direction and Y-direction, respectively. In the example of FIG. 3, smear preparation apparatus 300 has a square external shape along the X-direction and Y-direction in a planar view. It is also assumed that the X-direction is a width direction (or lateral direction) of smear preparation apparatus 300 and the Y-direction is a depth direction of smear preparation apparatus 300. The Y1-direction side is the front side of the apparatus, while the Y2-direction side is the back side of the apparatus. Moreover, it is assumed that a vertical direction perpendicular to the horizontal plane is a Z-direction.

Sample containers 211, each containing a sample, can be installed in sample transporter 210. Sample transporter 210 transports installed sample containers 211 to a predetermined pickup position. Sample transporter 210 transports rack 212 holding sample containers 211, for example. Aspirator 220 aspirates a liquid sample such as blood and urine from each of sample containers 211 transported to the pickup position by sample transporter 210. Aspirator 220 feeds the aspirated sample to smear unit 110.

In the configuration example of FIG. 3, slide feeder 20 includes first feeder 21 and second feeder 22. Slide feeder 20 may include one or three or more feeders. Slide feeder 20 can house slide glasses 10 in an unused state before smearing of the sample in first feeder 21 and second feeder 22. Slide glasses 10 are housed flat with their smear surfaces facing upward in first feeder 21 and second feeder 22. Slide feeder 20 is configured to hold slide glasses 10 in a state where the long-side direction of slide glass 10 corresponds to the Y-direction and the short-side direction of slide glass 10 corresponds to the X-direction.

First feeder 21 and second feeder 22 have substantially the same configuration. First and second feeders 21 and 22 are arranged side by side in the X-direction. First and second feeders 21 and 22 can each feed slide glasses 10 before smearing housed therein, one by one, by moving slide glasses 10 in the Y2-direction.

In the configuration example of FIG. 3, slide transporter 50 is provided to transport slide glass 10 while moving between slide feeder 20, removal mechanism 120, print processor 30, and smear processor 40. More specifically, slide transporter 50 works as a transporter shared among slide feeder 20, removal mechanism 120, print processor 30, and smear processor 40.

Slide transporter 50 can receive slide glass 10 from first feeder 21. Slide transporter 50 can also receive slide glass 10 from second feeder 22. Slide transporter 50 can transport held slide glass 10 to respective processing positions in removal mechanism 120, print processor 30, and smear processor 40. Slide transporter 50 transports slide glass 10 received from slide feeder 20 to removal mechanism 120, print processor 30, and smear processor 40 in this order. In a state of being held by slide transporter 50, slide glass 10 is subjected to predetermined processing in each of removal mechanism 120, print processor 30, and smear processor 40.

In the configuration example of FIG. 3, slide transporter 50 transports slide glass 10 in a state where the long-side direction of slide glass 10 corresponds to the Y2-direction and the short-side direction of slide glass 10 corresponds to the X-direction.

Removal mechanism 120 removes extraneous matter adhering to the surface of slide glass 10. In the configuration example of FIG. 3, removal mechanism 120 is arranged on the Y2-direction side of slide feeder 20. Removal mechanism 120 performs extraneous matter removal processing on slide glass 10 held on the upper surface of slide transporter 50. The extraneous matter is, for example, small foreign matter such as glass powder and dust.

In the configuration example of FIG. 3, print processor 30 is arranged on the Y2-direction side of slide feeder 20. Print processor 30 is arranged on the Y2-direction side of removal mechanism 120. Print processor 30 can print various kinds of information such as sample information in print region 12 on slide glass 10. Also, print processor 30 performs printing on slide glass 10 held on the upper surface of slide transporter 50.

In the configuration example of FIG. 3, smear processor 40 is arranged on the X1-direction side of print processor 30. Smear processor 40 can smear the sample in smear region 11 on slide glass 10. Smear processor 40 smears the sample on slide glass 10 held on the upper surface of slide transporter 50.

In the configuration example of FIG. 3, discharge mechanism 140 discharges slide glass 10, which is transported to smear processor 40, to first drying processor 130. Discharge mechanism 140 is provided to extend in the Y-direction, and can transport slide glass 10 in the Y1-direction. Discharge mechanism 140 places slide glass 10, which is transported to smear processor 40, at a processing position in first drying processor 130 by moving slide glass 10 in the Y1-direction.

First drying processor 130 receives slide glass 10 with the sample smeared thereon from smear processor 40, and to blow air to smear region 11 on slide glass 10. First drying processor 130 can dry the sample smeared on slide glass 10 by blowing air.

In the configuration example of FIG. 3, discharge mechanism 140 is configured to further discharge slide glass 10, which is discharged to first drying processor 130, to transport mechanism 150 from first drying processor 130. Discharge mechanism 140 passes slide glass 10, which is transported to first drying processor 130, to transport mechanism 150 by moving slide glass 10 in the Y1-direction.

Transport mechanism 150 is arranged on the Y1-direction side of first drying processor 130 and stain processor 160, and is provided to extend in the X-direction. Transport mechanism 150 transports slide glass 10 in the X1-direction from first drying processor 130 to pickup position 410 between stain processor 160 and slide setup unit 170. Transport mechanism 150 includes accommodation unit 151 that accommodates slide glass 10, and can move accommodation unit 151 in the X-direction. Transport mechanism 150 receives slide glass 10 laid approximately parallel to the installation surface into accommodation unit 151, and transports slide glass 10 to pickup position 410 while setting slide glass 10 up approximately perpendicularly to the installation surface. At pickup position 410, slide glass 10 is held upright such that the smear surface is set in the vertical direction (Z-direction). Slide glass 10 transported to pickup position 410 is transported to stain processor 160 or slide setup unit 170.

Stain processor 160 is configured to stain the sample smeared on slide glass 10. Stain processor 160 is arranged on the X1-direction side of first drying processor 130. Stain processor 160 is arranged on the Y2-direction side of pickup position 410. Stain processor 160 is provided to extend in the Y-direction. Stain processor 160 includes a stain tank for storing a staining solution and a cleaning tank for storing a cleaning liquid. Stain processor 160 performs stain processing and cleaning processing on smeared slide glass 10 in the stain tank and the cleaning tank.

Slide setup unit 170 is arranged on the Y1-direction side of stain processor 160, and is configured to hold slide glass 10 such that slide glass 10 can be taken in and out. Slide setup unit 170 includes slide storage container 240, for example, and holds slide glasses 10 in slide storage container 240.

Transport mechanism 180 can transport slide glass 10 between stain processor 160, slide setup unit 170, and pickup position 410. Transport mechanism 180 can be moved in the X-direction, Y-direction, and Z-direction at a height position above stain processor 160, slide setup unit 170, and pickup position 410, for example. Thus, transport mechanism 180 can pick up slide glass 10 arranged at each of stain processor 160, slide setup unit 170, and pickup position 410, and can transport slide glass 10 to each of stain processor 160, slide setup unit 170, and pickup position 410.

In smear preparation apparatus 300, transport mechanism 180 can transport slide glass 10 subjected to the print processing and smear processing in smear unit 110 not only from pickup position 410 to stain processor 160 but also from pickup position 410 to slide setup unit 170. Moreover, smear preparation apparatus 300 can transport slide glass 10 with the sample smeared thereon, which is manually placed in slide setup unit 170 by a user, to stain processor 160 from slide setup unit 170.

In the configuration example of FIG. 3, transport mechanism 180 can transport slide glass 10 to second drying processor 190 and slide storage unit 200.

In the configuration example of FIG. 3, second drying processor 190 is arranged on the Y2-direction side of stain processor 160. Second drying processor 190 dries slide glass 10, which is stained by stain processor 160, by blowing air, for example.

Slide storage unit 200 receives and store processed slide glass 10. In the configuration example of FIG. 3, slide storage unit 200 is arranged on the X1-direction side of second drying processor 190.

For example, slide storage containers 240 can be placed in slide storage unit 200. Also, slide storage unit 200 can transport slide storage containers 240 placed therein. Slide storage unit 200 holds slide glasses 10 in slide storage container 240.

Controller 230 includes unillustrated CPU and memory, and controls operations of the respective units in smear preparation apparatus 300. Controller 230 includes output unit 231. Output unit 231 is a display unit such as a liquid crystal monitor, for example.

With such a configuration, smear preparation apparatus 300 can automatically prepare smears by performing the print processing, sample smear processing, and stain processing on slide glass 10.

(Configuration of Slide Transporter)

Figure 4:
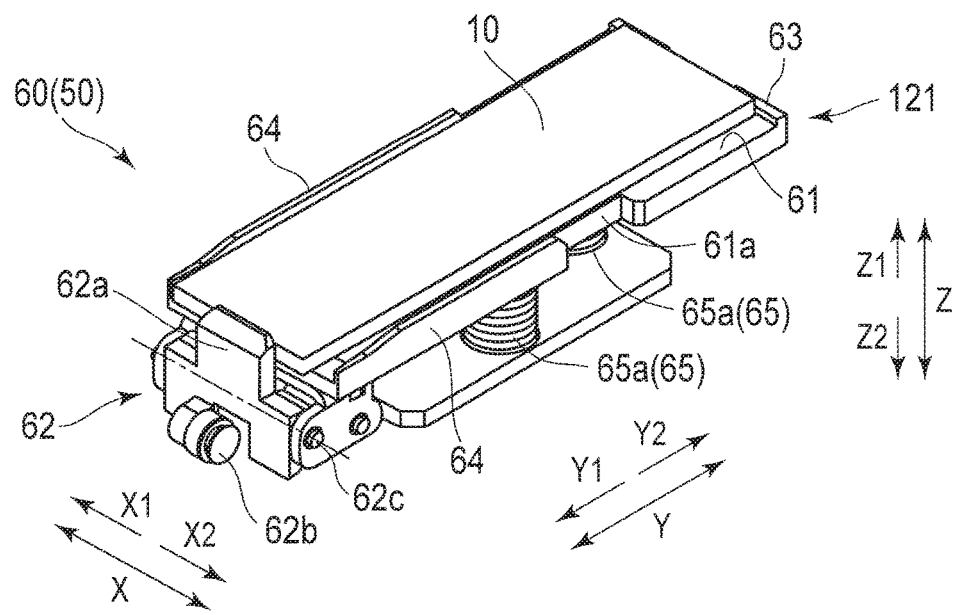
FIG. 4 is a perspective view illustrating a configuration example of the slide holder mechanism in the smear preparation apparatus in FIG. 3.
Figure 5:
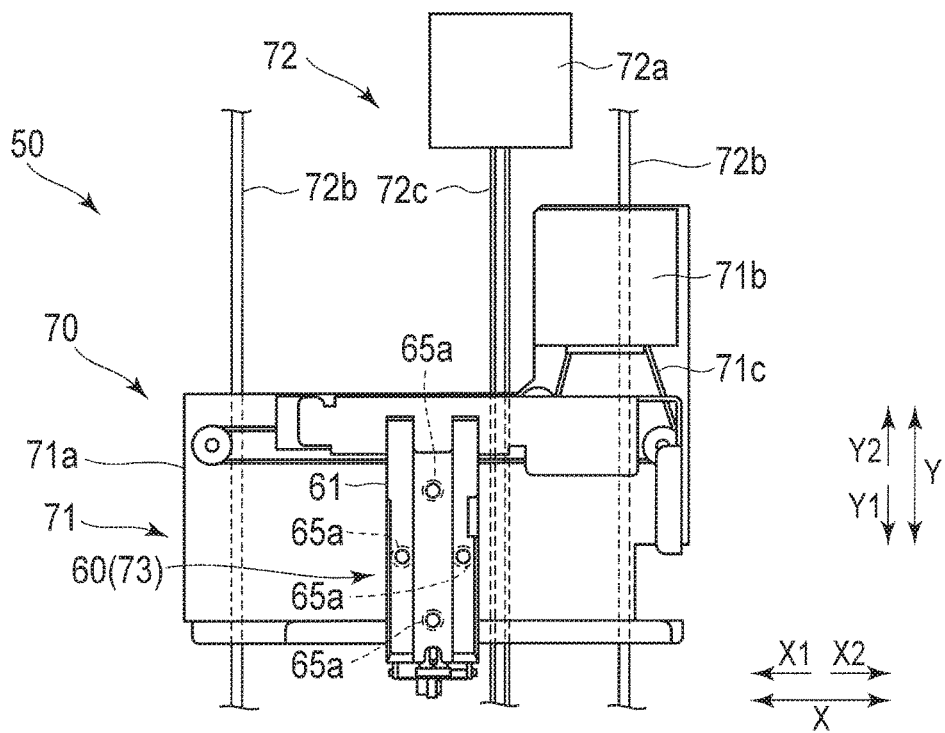
FIG. 5 is a plan view illustrating a specific configuration example of a slide transporter.
Figure 6:
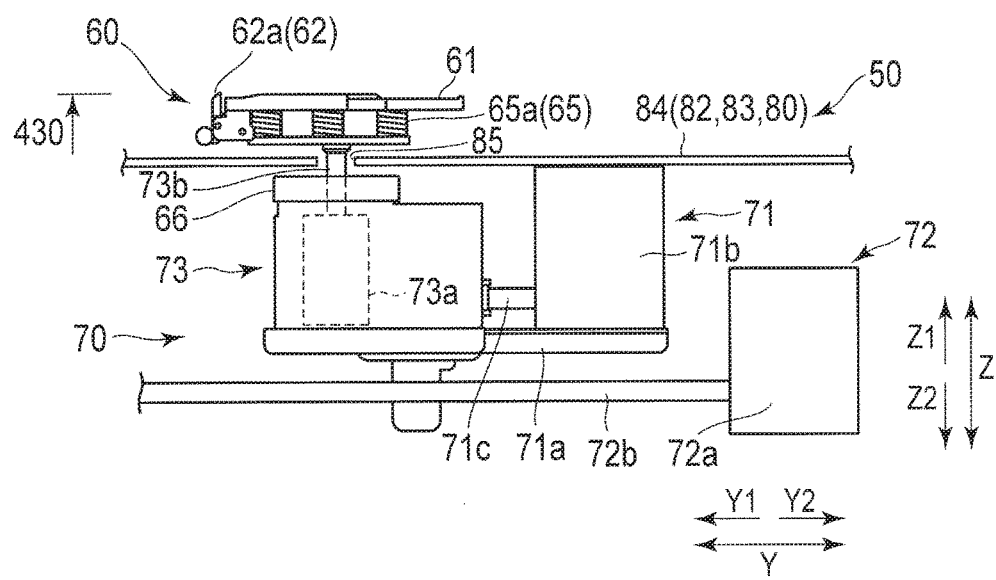
FIG. 6 is a side view illustrating a specific configuration example of the slide transporter.

Next, with reference to FIGS. 4 to 6, a configuration example of slide transporter 50 is described.

FIG. 4 illustrates a configuration example of slide holder mechanism 60 in slide transporter 50. In this configuration example, slide holder mechanism 60 includes mount plate 61, catcher 62, abutting part 63, and wall parts 64.

Slide holder mechanism 60 is configured to be able to mount and hold slide glass 10 on an upper surface of mount plate 61. To be more specific, slide holder mechanism 60 holds slide glass 10 on the upper surface of mount plate 61 in a flat placement state where a smear surface of slide glass 10 faces upward. Mount plate 61 forms the upper surface of slide holder mechanism 60. Mount plate 61 is formed in a plate shape extending in the horizontal direction (XY-direction). Mount plate 61 supports slide glass 10 from below (Z2-direction side). Slide transporter 50 can use transfer mechanism 70 to move slide holder mechanism 60 holding slide glass 10 on the upper surface thereof to print processor 30 and smear processor 40.

Catcher 62 includes press part 62a, switch part 62b, and rotary shaft 62c. Catcher 62 can be moved between an open position (see FIG. 11) where slide glass 10 can be taken in and out and a catch position (see FIG. 6) where slide glass 10 is held. Catcher 62 can hold slide glass 10 so as not to move on slide holder mechanism 60.

In the configuration example illustrated in FIG. 4, catcher 62 is arranged on the Y1-direction side of slide holder mechanism 60. Also, abutting part 63 is provided to protrude upward at the Y2-direction side end on the upper surface of mount plate 61. Catcher 62 can be rotated to the Y1-direction side and the Y2-direction side about rotary shaft 62c extending in the X-direction. Catcher 62 uses an unillustrated spring member to pull press part 62a to the Y2-direction side. Thus, catcher 62 catches the short side of slide glass 10 in the longitudinal direction by pressing the end face of slide glass 10 on the upper surface of mount plate 61 against abutting part 63 on the Y2-direction side.

Press part 62a is arranged above (on the Z1-direction side of) rotary shaft 62c. Switch part 62b is arranged below (on the Z2-direction side of) rotary shaft 62c. Catcher 62 can be rotated to the Y1-direction side about rotary shaft 62c against tensile force of the spring member by pushing switch part 62b to the Y2-direction side. With such a configuration, catcher 62 can be moved between the open position where slide glass 10 can be taken in and out by press part 62a retreating below the upper surface of mount plate 61 and the catch position where slide glass 10 is held by press part 62a protruding above the upper surface of mount plate 61.

Moreover, slide holder mechanism 60 includes wall parts 64 for regulating movement of slide glass 10 placed on slide holder mechanism 60. Wall parts 64 are provided in a pair on either end of slide holder mechanism 60 in the X-direction. More specifically, a pair of wall parts 64 are provided on the ends in the short-side direction perpendicular to the long-side direction in which catcher 62 catches slide glass 10.

In the configuration example of FIG. 4, notch part 61a extending for a predetermined length in the X1-direction is provided on the X2-direction side end of slide holder mechanism 60. Slide glass 10 on the upper surface of mount plate 61 can be moved to the X1-side by moving an unillustrated press part in the X1-direction from the X2-direction side of slide holder mechanism 60 to the inside of notch part 61a. Thus, slide glass 10 on slide holder mechanism 60 can be positioned in the X-direction by the end face of slide glass 10 coming into contact with wall part 64 on the X1-side. Note that slide glass 10 on slide holder mechanism 60 is positioned in the Y-direction by catcher 62 brining the end face of slide glass 10 into contact with abutting part 63.

In the configuration example of FIG. 4, slide holder mechanism 60 includes resilient elastic body 65 for supporting the lower surface side of mount plate 61. Elastic body 65 supports the lower surface side of mount plate 61 such that elastic body 65 can extend and contract in the vertical direction. Thus, when the print processing or the smear processing is performed on slide glass 10 on mount plate 61, the position of slide glass 10 can be fine-adjusted with elastic body 65 extended or contracted along with application of pressure to slide glass 10. This absorbs a variation in thickness of slide glass 10, and enables print quality and smear state to be stabilized.

In a configuration example illustrated in FIG. 5, elastic bodies 65 are provided at predetermined intervals along the longitudinal direction of mount plate 61. Thus, even when a height position of a printer for print processing or a smear member for smear processing is slightly different from a height position of the surface of slide glass 10, the long-side of slide glass 10 can be inclined according to the height position of the counterpart by deforming elastic bodies 65. As a result, print quality and smear state can be stabilized by absorbing a deviation in height position attributable to an assembly error and the like. Elastic bodies 65 may be cushion materials such as rubber.

In the configuration example illustrated in FIG. 5, three or more elastic bodies 65 are provided to surround the center of gravity of mount plate 61, and each include spring members 65a that support the lower surface of mount plate 61. Thus, even when the printer for print processing or the smear member for smear processing is inclined with respect to the surface of slide glass 10 due to the assembly error and the like, the posture of slide glass 10 can be fine-adjusted with spring members 65a extended or contracted such that the printer or the smear member comes into surface contact with the surface of slide glass 10. As a result, the print quality and smear state can be stabilized by absorbing a deviation in posture attributable to the assembly error and the like.

In the configuration example illustrated in FIG. 5, the center of gravity of mount plate 61 may be considered as the center of mount plate 61 having an approximately rectangular shape in a planar view. Spring members 65a are provided such that two thereof are arranged at a predetermined interval in the long-side direction (Y-direction) of held slide glass 10 and the other two thereof are arranged at a predetermined interval in the short-side direction (X-direction) thereof. Two spring members 65a in the long-side direction (Y-direction) are arranged on either side of the center of mount plate 61 in the long-side direction. Meanwhile, two spring members 65a in the short-side direction (X-direction) are arranged on either side of the center of mount plate 61 in the short-side direction. Therefore, four spring members 65a are arranged in total at vertices of a rhombus shape surrounding the center of gravity of mount plate 61.

Figure 16:
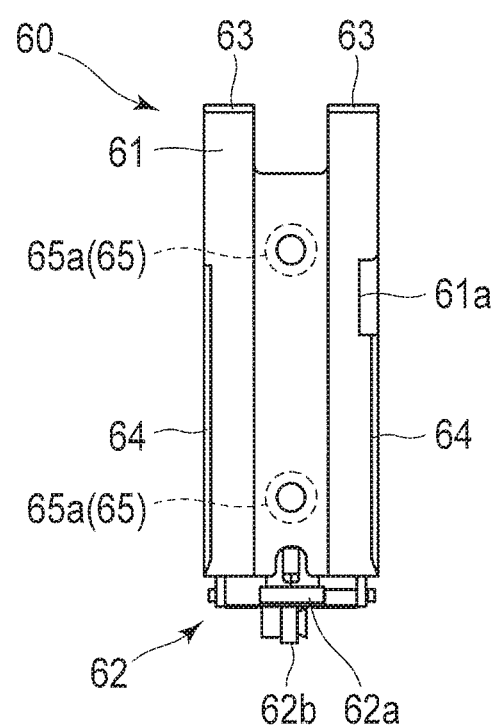
FIG. 16 is a plan view illustrating another arrangement example of elastic bodies in the slide holder mechanism.

Note that, although four elastic bodies 65 are provided in the configuration example illustrated in FIG. 5, two elastic bodies 65, for example, may be provided at a predetermined interval along the long-side direction of mount plate 61 as illustrated in FIG. 16. Alternatively, one, three, or five or more elastic bodies 65 may be provided.

(Configuration of Transfer Mechanism in Slide Transporter)

In a configuration example illustrated in FIGS. 5 and 6, transfer mechanism 70 in slide transporter 50 includes first transfer mechanism 71, second transfer mechanism 72, and third transfer mechanism 73. First transfer mechanism 71 can move held slide glass 10 in the X-direction. Second transfer mechanism 72 can move held slide glass 10 in the Y-direction. Third transfer mechanism 73 can move held slide glass 10 in the Z-direction. Thus, transfer mechanism 70 can move slide mechanism 60 holding slide glass 10 in the XY-direction within the horizontal plane and in the vertical direction (Z-direction).

First transfer mechanism 71 includes a belt-driven direct operated mechanism including base part 71a, motor 71b, belt 71c, and an unillustrated rail. Second transfer mechanism 72 includes a belt-driven direct operated mechanism including motor 72a, a pair of rails 72b, and belt 72c.

In the configuration example of FIG. 6, transfer mechanism 70 includes air cylinder 73a for moving slide holder mechanism 60 in the vertical direction. More specifically, third transfer mechanism 73 includes an air-driven mechanism including air cylinder 73a. Thus, the apparatus configuration can be simplified compared with a case where third transfer mechanism 73 includes a servo motor and the like to move slide holder mechanism 60 in the vertical direction, for example. Here, it is difficult for air cylinder 73a itself to accurately control the position in the vertical direction. However, the need for accurate positional control to be performed on transfer mechanism 70 side is eliminated by providing vertical positioning members 80 for positioning by coming into contact with the predetermined portions of slide holder mechanism 60 or slide glass 10. Therefore, the configuration of transfer mechanism 70 can be simplified by using air cylinder 73a while ensuring positioning accuracy.

Third transfer mechanism 73 for moving slide holder mechanism 60 in the vertical direction may be configured using, for example, a combination of a motor and a direct operated mechanism, a linear motor mechanism, or an actuator such as a solenoid, other than the air-driven mechanism including air cylinder 73a. Note that vertical positioning of slide holder mechanism 60 or slide glass 10 on slide holder mechanism 60 is described later.

Slide holder mechanism 60 is supported to be movable in the vertical direction by air cylinder 73a. Air cylinder 73a can extend and contract column part 73b in the vertical direction (Z-direction). Column part 73b includes a piston rod of air cylinder 73a. Slide holder mechanism 60 is attached to column part 73b through elastic bodies 65 provided on an upper end of column part 73b.

Third transfer mechanism 73 is supported to be movable in the X-direction by first transfer mechanism 71. Motor 71b, belt 71c, and the rail in first transfer mechanism 71 are arranged on base part 71a. Belt 71c is rotated by drive motor 71b, and thus slide holder mechanism 60 is moved in the X-direction together with third transfer mechanism 73. Base part 71a is installed above rail 72b in second transfer mechanism 72, and can be moved in the Y-direction.

First transfer mechanism 71 is supported to be movable in the Y-direction by second transfer mechanism 72. Second transfer mechanism 72 can move slide holder mechanism 60 in the Y-direction by moving base part 71a in the Y-direction. To be more specific, belt 72c is rotated by drive motor 72a, and thus slide holder mechanism 60, third transfer mechanism 73, and first transfer mechanism 71 are all moved in the Y-direction.

In the configuration example of FIG. 6, slide holder mechanism 60 includes contact member 66 that is lifted by transfer mechanism 70 together with mount plate 61. Contact member 66 is arranged below (in the Z2-direction) mount plate 61. Contact member 66 works as the predetermined portion 60a of slide holder mechanism 60 illustrated in FIG. 2. Contact member 66 is configured to perform vertical positioning of slide holder mechanism 60 by coming into contact with flat plate member 84 to be described later in vertical positioning member 80.

Slide holder mechanism 60 can be moved to lowered position 430 and lifted positions, which are set by vertical positioning member 80, by air cylinder 73a. At lowered position 430, contact member 66 is arranged at a position separated downward (in the Z2-direction) from flat plate member 84.

(Smear Processor)

Figure 7:
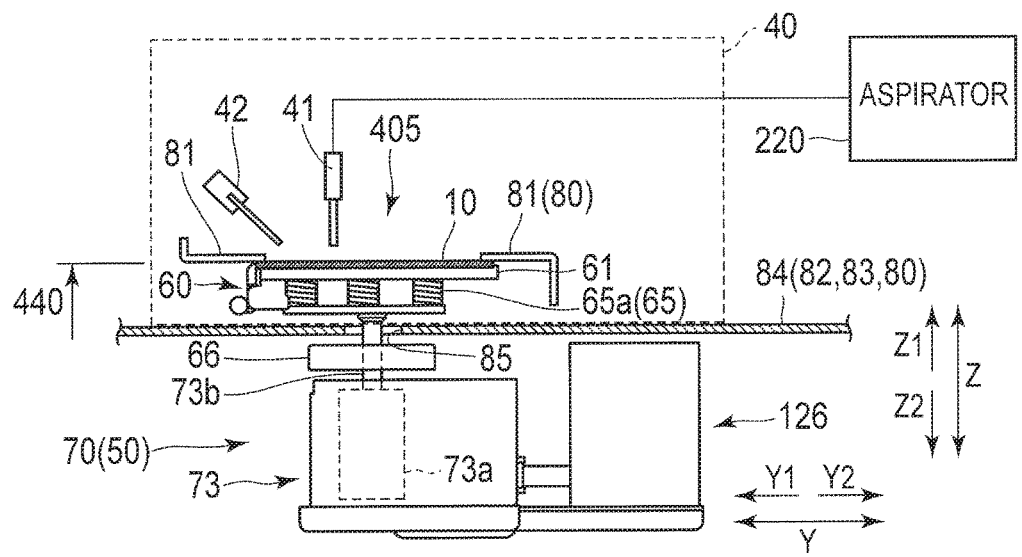
FIG. 7 is a schematic side view illustrating a smear processor and the slide transporter.

In a configuration example of FIG. 7, smear processor 40 includes drop unit 41 and smear member 42. Drop unit 41 drops a sample on transported slide glass 10. Smear member 42 smears the dropped sample on slide glass 10.

In the configuration example of FIG. 7, drop unit 41 is configured to drop the sample on slide glass 10 on slide holder mechanism 60. Smear member 42 is configured to smear the dropped sample by coming into contact with slide glass 10 on slide holder mechanism 60. Thus, in smear processor 40, the sample can be dropped and smeared directly on slide glass 10 on slide holder mechanism 60 transported by slide transporter 50. As a result, smear processor 40 can quickly perform smear processing of the sample. Moreover, slide glass 10 on slide holder mechanism 60 can be positioned by vertical positioning member 80. Thus, the smear processing can be accurately performed on slide glass 10 on slide holder mechanism 60.

Drop unit 41 and smear member 42 are both arranged at positions above slide glass 10 transported by slide transporter 50. Smear member 42 is, for example, a drawing glass. Smear member 42 can be moved in the vertical direction (Z-direction) and in the Y-direction by an unillustrated transfer mechanism. In the configuration example of FIG. 7, slide holder mechanism 60 in slide transporter 50 can be moved in the XY-direction. This eliminates the need for providing a mechanism to move smear member 42 in the X-direction. Drop unit 41 is fluidically connected to aspirator 220, and includes a nozzle for discharging the sample aspirated by aspirator 220. Drop unit 41 can be moved in the X-direction (direction perpendicular to the page space of FIG. 7), for example, by an unillustrated transfer mechanism.

Slide transporter 50 is moved in the horizontal direction at lowered position 430 (see FIG. 6), thereby positioning slide holder mechanism 60 at processing position 405 in smear processor 40 from print processor 30 side. As illustrated in FIG. 7, slide transporter 50 uses transfer mechanism 70 to lift slide holder mechanism 60 at processing position 405 in smear processor 40.

In the configuration example of FIG. 7, vertical positioning member 80 includes first positioning member 81 provided in smear processor 40. First positioning member 81 is arranged at smear height position 440 for smearing the sample on slide glass 10. First positioning member 81 comes into contact with slide glass 10 lifted by transfer mechanism 70, thereby positioning the surface of slide glass 10 at smear height position 440. Thus, the vertical positioning to smear height position 440 can be performed based on the upper surface position of slide glass 10. Therefore, the upper surface of slide glass 10 can be accurately aligned to smear height position 440 regardless of a variation in thickness of slide glass 10.

First positioning member 81 includes a metal plate-like member, for example. First positioning member 81 is fixed to a housing (not illustrated) of smear preparation apparatus 300, a chassis portion included in smear processor 40, or the like, for example, in a state of being aligned to smear height position 440.

Figure 8:
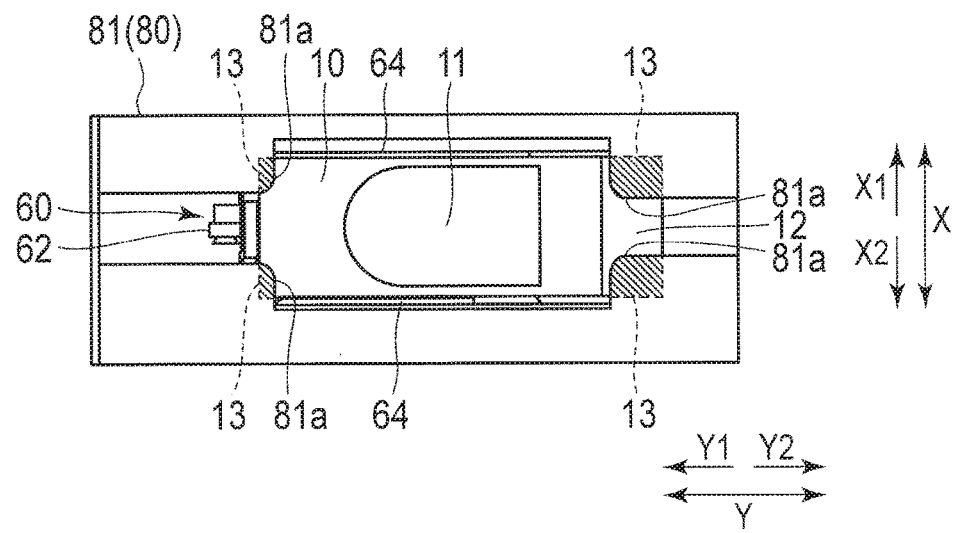
FIG. 8 is a schematic plan view for explaining a first positioning member and a slide glass.

FIG. 8 is a plan view illustrating a shape example of first positioning member 81. In the configuration example of FIG. 8, first positioning member 81 is arranged to come into contact with corners 13 of the upper surface of slide glass 10 lifted by transfer mechanism 70. Thus, even when first positioning member 81 is provided to come into direct contact with the upper surface of slide glass 10, first positioning member 81 does not interfere with the smear processing. In FIG. 8, contact portions between first positioning member 81 and the upper surface of slide glass 10 in a planar view are illustrated by hatching. First positioning member 81 comes into contact, from above, with corners 13 outside smear region 11 in a state where smear region 11 on the upper surface of slide glass 10 is exposed.

In the configuration example of FIG. 8, first positioning member 81 is configured to come into contact with four corners of the upper surface of slide glass 10 lifted by transfer mechanism 70. Thus, not only the height position of slide glass 10 but also the posture of slide glass 10 can be accurately maintained constant. Therefore, even when the smear processing is performed using smear member 42, the end face of smear member 42 and the upper surface of slide glass 10 can be allowed to come into parallel contact with each other so as to achieve surface contact or line contact as much as possible. Thus, stable smear quality can be achieved. First positioning member 81 includes four contact portions 81a, which come into contact with four corners 13 of slide glass 10, respectively.

More specifically, a minute difference in inclination between first positioning member 81 and slide glass 10 is absorbed by deformation of elastic bodies 65 supporting slide holder mechanism 60. Thus, a contact state between first positioning member 81 and slide glass 10 is ensured. As a result, parallelism between the end face of smear member 42 and smear region 11 on slide glass 10 is ensured.

In a state of being set at smear height position 440 by first positioning member 81, smear processor 40 performs smear processing on slide glass 10 held on slide holder mechanism 60. Smear processor 40 drops the sample onto smear region 11 by moving drop unit 41 to above smear region 11. Then, smear processor 40 allows the end face of smear member 42 to come into contact with droplets of the sample, and moves smear member 42 in the long-side direction (Y-direction) of slide glass 10, thereby smearing the sample in smear region 11.

As described above, in smear processor 40 that particularly requires accuracy because of the use of smear member 42 such as a drawing glass, the upper surface of slide glass 10 itself comes into contact with first positioning member 81. Thus, the vertical positioning to smear height position 440 is performed based on the upper surface position of slide glass 10. Therefore, the upper surface of slide glass 10 can be accurately aligned to smear height position 440 even when there is an individual difference in thickness between slide glasses 10. As a result, a variation in smear quality attributable to such a difference in thickness between slide glasses 10 can be effectively suppressed.

(Print Processor)

Figure 9:
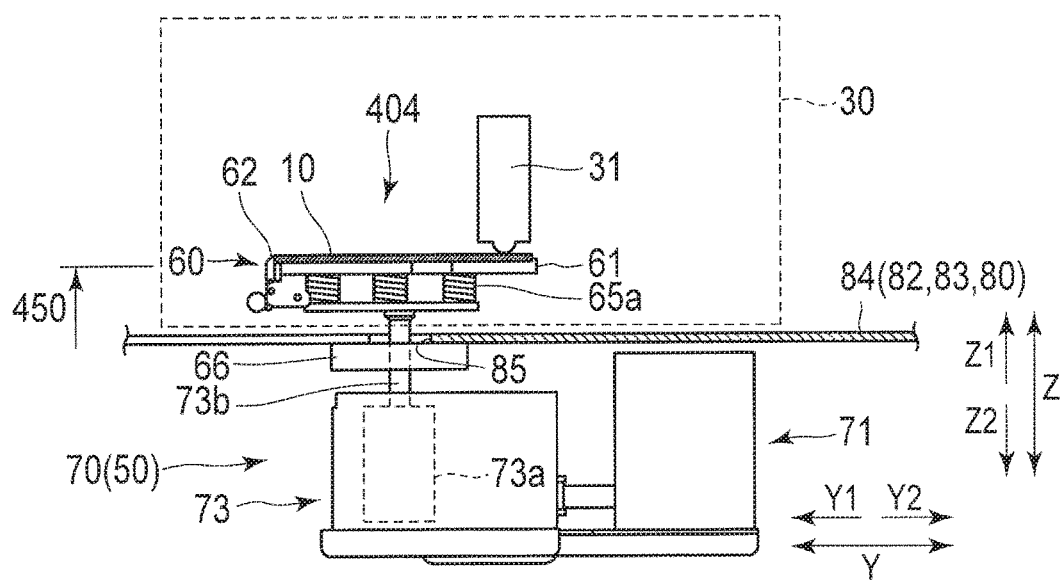
FIG. 9 is a schematic side view illustrating a print processor and the slide transporter.

In a configuration example of FIG. 9, print processor 30 includes printer 31. Printer 31 is arranged at a position above slide glass 10 transported by slide transporter 50. Printer 31 is configured to perform printing by coming into contact with slide glass 10 on slide holder mechanism 60. Thus, print processor 30 can perform printing directly on slide glass 10 on slide holder mechanism 60. Therefore, print processor 30 can quickly perform the print processing. Moreover, vertical positioning member 80 can position slide glass 10 on slide holder mechanism 60. Thus, print quality can be ensured even when printer 31 comes into direct contact with slide glass 10 on slide holder mechanism 60.

Printer 31 is a thermal-transfer printer, for example. Printer 31 includes a print head at its lower end, and is configured to be movable in the vertical direction (Z-direction). In the configuration example of FIG. 9, slide holder mechanism 60 in slide transporter 50 can be moved in the XY-direction. This eliminates the need for providing an XY-direction transfer mechanism in printer 31.

Slide transporter 50 is moved in the horizontal direction at lowered position 430 (see FIG. 6) where slide holder mechanism 60 is lowered, thereby positioning slide holder mechanism 60 at processing position 404 in print processor 30 from slide feeder 20 side. Slide transporter 50 uses transfer mechanism 70 to lift slide holder mechanism 60 at processing position 404 in print processor 30.

In the configuration example of FIG. 9, vertical positioning member 80 includes second positioning member 82 provided in print processor 30. Second positioning member 82 is arranged below slide glass 10 held by mount plate 61. Second positioning member 82 comes into contact with contact member 66 lifted by transfer mechanism 70, thereby locating mount plate 61 at print height position 450 of slide glass 10. Thus, with a simple configuration in which second positioning member 82 and contact member 66 come into contact with each other, slide glass 10 on mount plate 61 can be aligned to print height position 450.

The lifted position of slide holder mechanism 60 can be set by contact member 66 coming into contact with second positioning member 82. At print height position 450 set by second positioning member 82, print processor 30 performs print processing on slide glass 10 held by slide holder mechanism 60.

Print processor 30 lowers printer 31 and presses the print head against print region 12 on slide glass 10. In this event, a minute difference in inclination between the print head and slide glass 10 is absorbed by deformation of elastic bodies 65 supporting slide holder mechanism 60. Thus, a contact state between the print head and print region 12 on slide glass 10 is ensured. Printer 31 can perform printing over the entire print region 12 by moving slide transporter 50 in the Y-direction in a state where downward pressing force is applied by the print head in printer 31.

In the configuration example of FIG. 9, as described above, contact member 66 is configured to be horizontally moved by transfer mechanism 70 in a contact state with second positioning member 82 during the print processing. Thus, a movement operation for printing can be performed using transfer mechanism 70 in slide transporter 50. This eliminates the need for providing a horizontal transfer mechanism in print processor 30. As a result, the configuration of print processor 30 can be simplified. Moreover, in the configuration example of FIG. 9, contact member 66 includes a resin member. Contact member 66 made of resin enables easy and stable horizontal movement of slide glass 10 while maintaining the contact state between contact member 66 and second positioning member 82. A resin material with good slide characteristics, such as POM (polyacetal), for example, is preferable as contact member 66. The good slide characteristics mean properties with a low friction coefficient and with resistance to abrasion.

Note that, in the configuration in which vertical positioning member 80 includes first positioning member 81 and second positioning member 82, smear height position 440 (see FIG. 7) is set lower than print height position 450 (see FIG. 9). Smear height position 440 where first positioning member 81 comes into contact with slide glass 10 is set to a height position between print height position 450 of slide glass 10 in a state where contact member 66 comes into contact with second positioning member 82 and the height position of slide glass 10 at lowered position 430. Therefore, when first positioning member 81 comes into contact with slide glass 10 in smear processor 40, contact member 66 does not come into contact with second positioning member 82 (see FIG. 7).

(Removal Mechanism)

Figure 10:
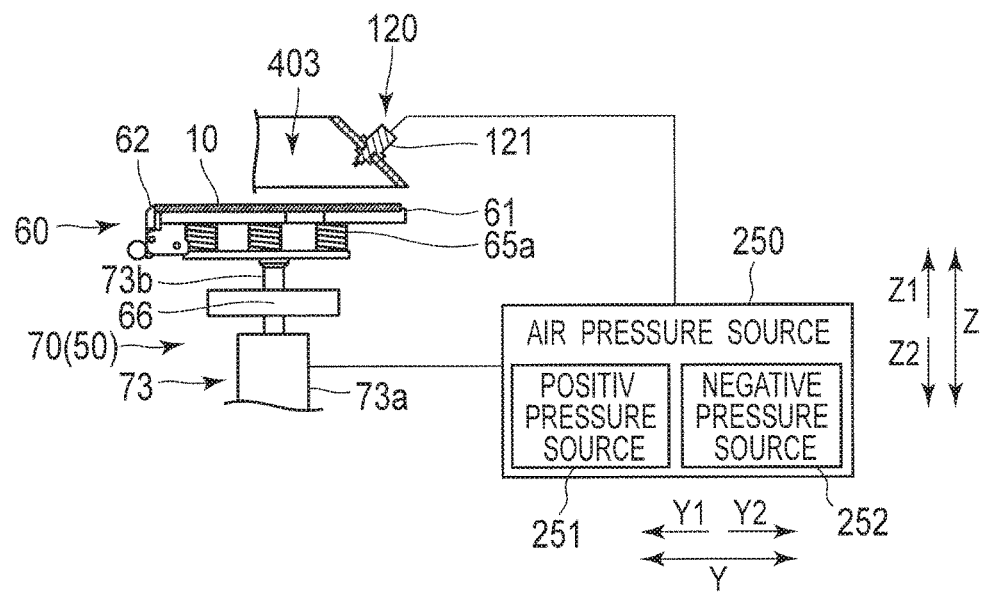
FIG. 10 is a schematic view for explaining configurations of a removal mechanism and the slide transporter.

In a configuration example of FIG. 10, removal mechanism 120 is configured to remove extraneous matter by emitting an air blast onto the surface of slide glass 10 held by slide holder mechanism 60. Removal mechanism 120 includes nozzle 121 for emitting an air blast. Nozzle 121 is arranged above slide holder mechanism 60 at a predetermined removal position, and is provided to emit an air blast obliquely downward. Slide transporter 50 locates slide holder mechanism 60 at the removal position from slide feeder 20 side at lowered position 430 (see FIG. 6) where slide holder mechanism 60 is lowered. Foreign matter on the surface of slide glass 10 is removed by the force of the air blast emitted onto the surface of slide glass 10 from nozzle 121. Note that FIG. 10 omits the illustration of the configurations of flat plate member 84 and transfer mechanism 70.

In the configuration example of FIG. 10, smear preparation apparatus 300 includes air pressure source 250 for supplying an air pressure to removal mechanism 120 and air cylinder 73a. Therefore, an air supply source for removal mechanism 120 and a drive source for air cylinder 73a are unified. Thus, the apparatus configuration can be simplified. Air pressure source 250 includes positive pressure source 251 for supplying a positive pressure and negative pressure source 252 for supplying a negative pressure. Removal mechanism 120 uses the positive pressure supplied from air pressure source 250 to emit an air blast onto slide glass 10. Air cylinder 73a uses the positive pressure supplied from air pressure source 250 to lift slide holder mechanism 60, and uses the negative pressure supplied from air pressure source 250 to lower slide holder mechanism 60.

(Slide Feeder)

Figure 11:
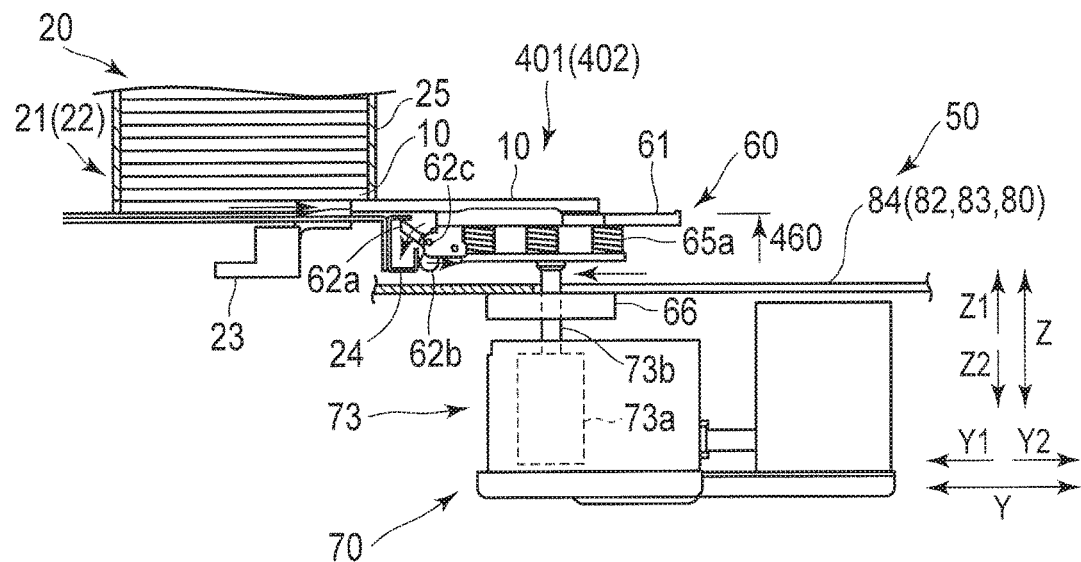
FIG. 11 is a schematic side view illustrating a slide feeder and the slide transporter.

In a configuration example of FIG. 11, slide feeder 20 includes: case part 25 for holding slide glasses 10 before processing in a stacked state; and discharger 23 which feeds slide glasses 10 by pushing slide glasses 10 stacked in case part 25, one by one, from case part 25. Thus, slide glasses 10 can be fed one by one while suppressing an installation area by stacking slide glasses 10.

First feeder 21 and second feeder 22 in slide feeder 20 each include case part 25 and discharger 23. Case part 25 has a hollow cylindrical shape extending in the vertical direction (Z-direction). Case part 25 has a rectangular parallelepiped external shape surrounding the perimeter of a predetermined number of slide glasses 10 stacked in the vertical direction.

Discharger 23 is provided below each of first feeder 21 and second feeder 22. Also, contact member 24 is provided at a hand-over position of slide glass 10. Slide transporter 50 is moved in the Y1-direction so that switch part 62b of catcher 62 comes into contact with contact member 24 arranged at the hand-over position of slide glass 10. Thus, press part 62a of catcher 62 is rotated about rotary shaft 62c and moved to the open position.

Discharger 23 is provided to protrude upward (in the Z1-direction) from the setup surface of slide glass 10. The protrusion amount of discharger 23 is smaller than the thickness of slide glass 10. Discharger 23 can be moved in the Y-direction by an unillustrated drive source such as a motor. In each of first feeder 21 and second feeder 22, slide glass 10 is pushed in the Y2-direction by discharger 23 and fed to slide transporter 50 in a state where catcher 62 is located at the open position. Discharger 23 discharges lowest slide glass 10 among the stacked slide glasses to slide transporter 50. Thus, slide glasses 10 can be fed one by one to slide transporter 50 from first feeder 21 or second feeder 22.

In the configuration example of FIG. 11, vertical positioning member 80 includes third positioning member 83 provided in slide feeder 20. Third positioning member 83 is configured to locate mount plate 61 at feed height position 460 of slide glass 10 by coming into contact with contact member 66 lifted by transfer mechanism 70. Thus, with a simple configuration in which third positioning member 83 and contact member 66 come into contact with each other, mount plate 61 can be aligned to feed height position 460. Therefore, slide glass 10 can be stably passed to slide transporter 50 from slide feeder 20 without providing an elevator mechanism or the like in slide feeder 20.

Here, in the configuration example illustrated in FIGS. 9 and 11, second positioning member 82 and third positioning member 83 are an integrally formed flat plate member 84. Print height position 450 and feed height position 460 are the same height position. More specifically, second positioning member 82 and third positioning member 83 are included in a common flat plate member 84. Thus, second positioning member 82 and third positioning member 83 can be unified. As a result, the configuration for positioning slide glass 10 in the vertical direction can be further simplified.

Flat plate member 84 is made of metal, for example, and is formed to extend in the horizontal direction. Flat plate member 84 is arranged at a predetermined height position so that mount plate 61 is arranged at print height position 450 and feed height position 460 in a contact state with contact member 66. Flat plate member 84 is arranged at a height position between transfer mechanism 70 and slide holder mechanism 60. Flat plate member 84 is fixed to an unillustrated housing of smear preparation apparatus 300, for example.

Figure 12:
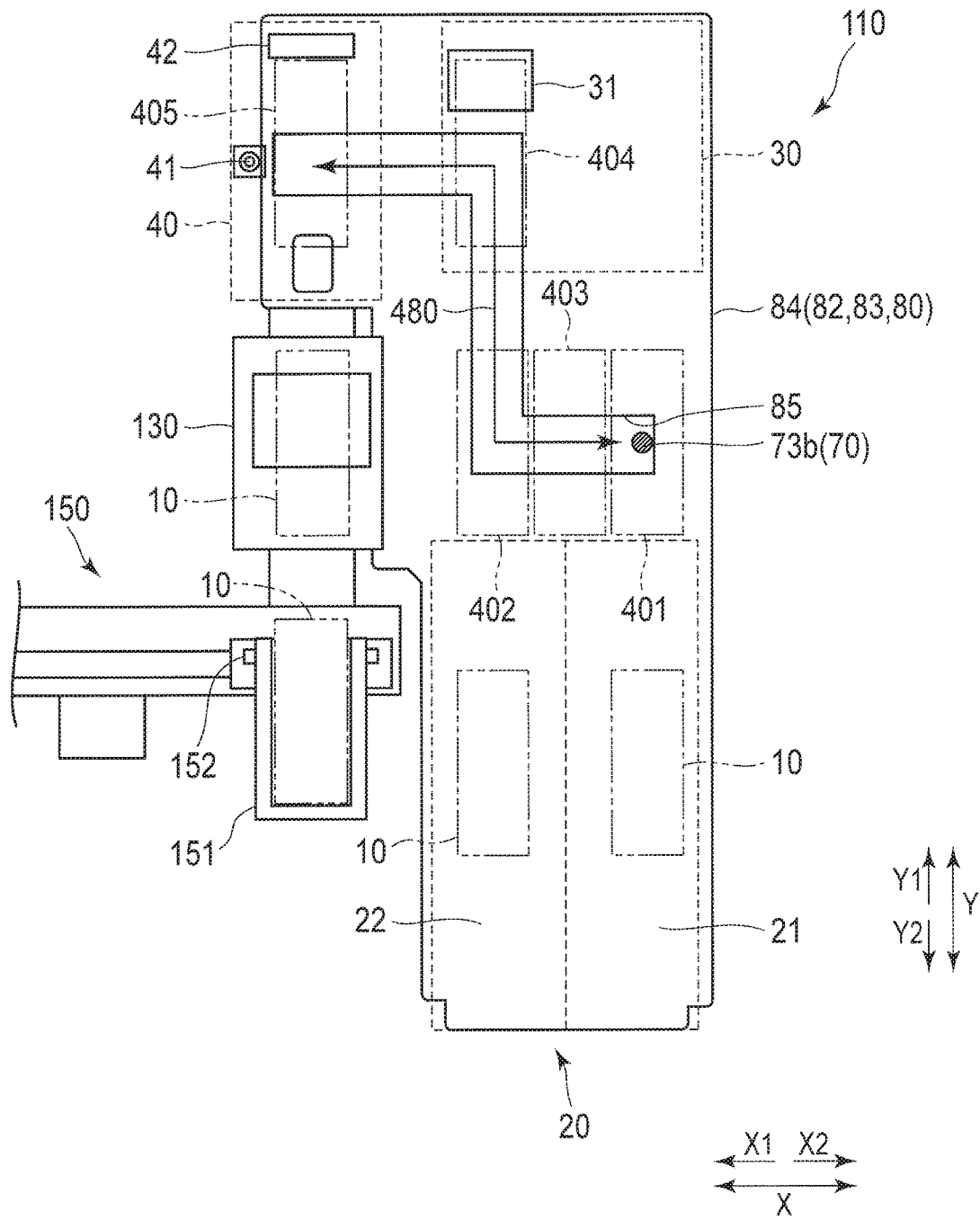
FIG. 12 is a plan view illustrating a slide glass transport path to the slide feeder, the removal mechanism, the print processor, and the smear processor.

In a configuration example of FIG. 12, flat plate member 84 is arranged to cover a horizontal movable range of transfer mechanism 70. Flat plate member 84 includes slit hole 85 provided along a movement path of slide holder mechanism 60. Also, column part 73b of transfer mechanism 70 is provided to vertically stand through slit hole 85 to support slide holder mechanism 60. Thus, even when flat plate member 84 is provided at the height position between transfer mechanism 70 and slide holder mechanism 60, flat plate member 84 does not interfere with the movement of slide holder mechanism 60. Moreover, small foreign matter such as glass powder and dust can be suppressed from dropping to transfer mechanism 70 side by flat plate member 84 covering the horizontal movable range of transfer mechanism 70 and thus receiving the foreign matter. In the configuration example of FIG. 12, flat plate member 84 is formed to cover the positions where slide feeder 20, print processor 30, smear processor 40, and removal mechanism 120 are provided.

Note that contact member 66 is formed in a plate-like shape that is too large to pass through slit hole 85 in a planar view. Therefore, even when slide holder mechanism 60 is lifted, contact member 66 is not moved to above flat plate member 84 through slit hole 85.

(Operations of Transfer Mechanism)

In the configuration example of FIG. 12, transfer mechanism 70 is configured to feed slide glass 10 onto the upper surface of slide holder mechanism 60 by moving slide holder mechanism 60 to slide feeder 20, and to locate slide glass 10 held by slide holder mechanism 60 to the respective height positions by horizontally moving slide holder mechanism 60 to print processor 30 and smear processor 40, in turn, and lifting slide glass 10 in print processor 30 and smear processor 40. Thus, common transfer mechanism 70 in slide transporter 50 can sequentially perform receiving of slide glass 10, print processing, and smear processing. As a result, the apparatus configuration can be simplified compared with a case where dedicated transfer mechanisms are provided in slide feeder 20, print processor 30, and smear processor 40, respectively.

To be more specific, slide feeder 20 (see FIG. 11) feeds slide glass 10 onto slide holder mechanism 60 at first feed position 401 for first feeder 21 or at second feed position 402 for second feeder 22. At removal position 403 aligned with first feed position 401 and second feed position 402 in the X-direction, removal mechanism 120 (see FIG. 10) performs extraneous matter removal processing on slide glass 10 held by slide holder mechanism 60. At processing position 404 located on the Y2-direction side of second feed position 402, print processor 30 (see FIG. 9) performs print processing on slide glass 10 held by slide holder mechanism 60. At processing position 405 located on the X1-direction side of processing position 404 for print processor 30, smear processor 40 (see FIG. 7) performs smear processing on slide glass 10 held by slide holder mechanism 60.

Thus, transfer mechanism 70 moves slide holder mechanism 60 along approximately Z-shaped path 480. Slit hole 85 in flat plate member 84 is formed into a shape corresponding to path 480. Along with the movement of slide holder mechanism 60, column part 73b that supports slide holder mechanism 60 is moved along path 480 on the inside of slit hole 85.

(First Drying Processor and Discharge Mechanism)

Figure 13:
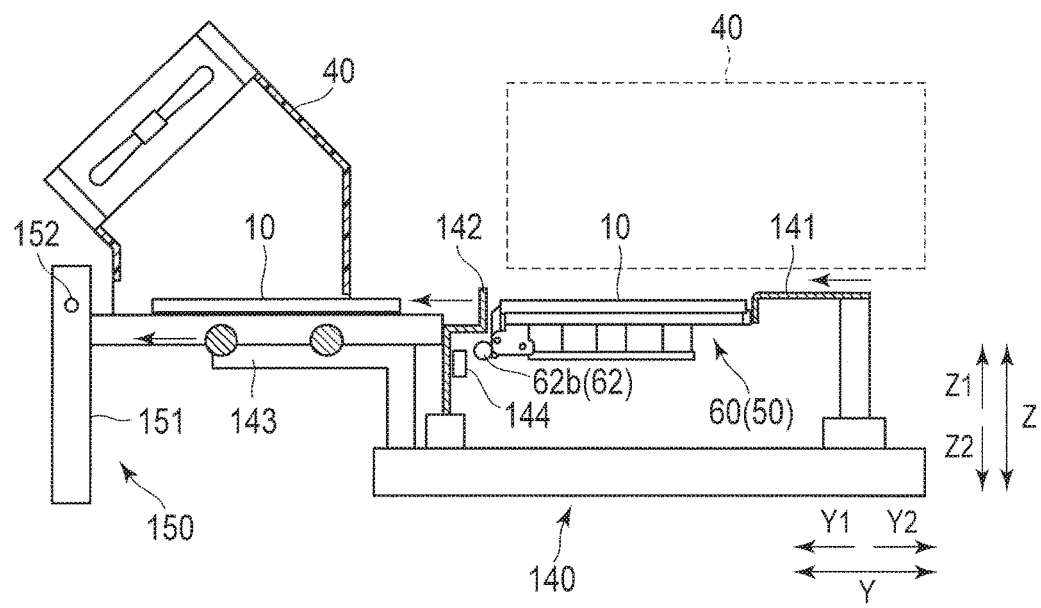
FIG. 13 is a schematic side view for explaining a first drying processor and a discharge mechanism.

In a configuration example of FIG. 13, discharge mechanism 140 is provided at the position where smear processor 40 is arranged. Discharge mechanism 140 can hand over slide glass 10 to first drying processor 130 by pushing slide glass 10 in the Y1-direction from slide transporter 50.

Discharge mechanism 140 is movable in the Y-direction. Discharge mechanism 140 includes first pusher 141. First pusher 141 can discharge slide glass 10 in the Y1-direction from slide transporter 50 positioned at smear processor 40 to first drying processor 130 by coming into contact with the Y2-direction side end face of slide glass 10.

In the configuration example of FIG. 13, discharge mechanism 140 includes second pusher 142, third pusher 143, and contact member 144. Second pusher 142 discharges slide glass 10 in first drying processor 130 to transport mechanism 150. Second pusher 142 is moved in the Y1-direction in a lifted state, thereby pushing slide glass 10 in first drying processor 130 toward transport mechanism 150. Also, second pusher 142 is moved in the Y2-direction in a lowered state, and thus returned to its original position while avoiding slide glass 10 on first drying processor 130.

Figure 14:
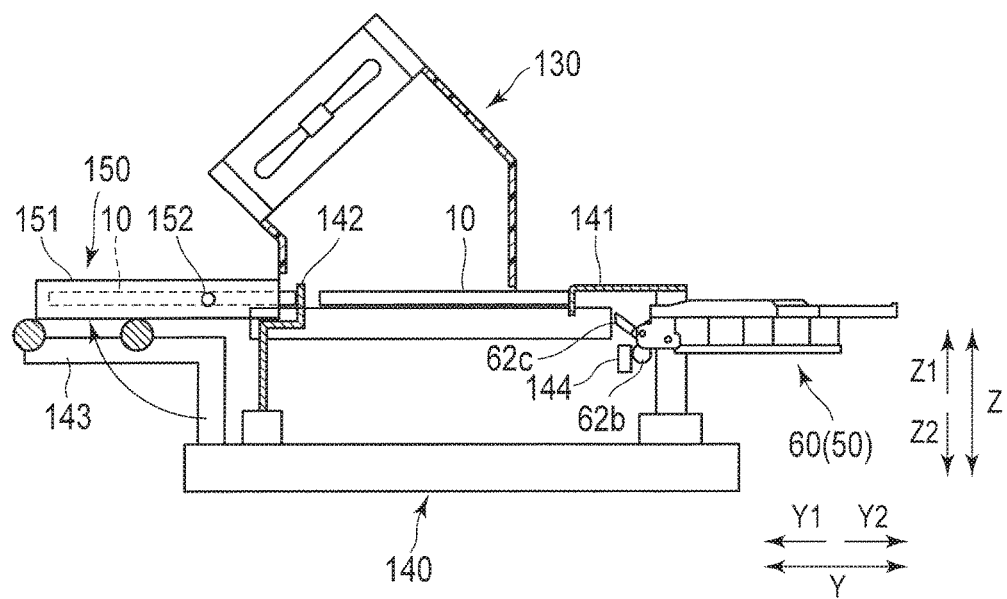
FIG. 14 is a side view for explaining handing over of slide glasses from the first drying processor to the transport mechanism.

Third pusher 143 can rotate transport mechanism 150 by pushing accommodation unit 151 in transport mechanism 150 in the Y1-direction. To be more specific, accommodation unit 151 in transport mechanism 150 can be rotated about rotary shaft 152 in the X-direction. As illustrated in FIG. 14, accommodation unit 151 in a horizontal posture receives slide glass 10 pushed in the Y1-direction by second pusher 142. Then, after receiving slide glass 10, accommodation unit 151 is set in a posture lone in the vertical direction under the force of gravity by third pusher 143 retreating in the Y2-direction.

Contact member 144 can move catcher 62 in slide transporter 50 to the open position by coming into contact with catcher 62.

(Smear Preparation Operation by Smear Preparation Apparatus)

Figure 15:
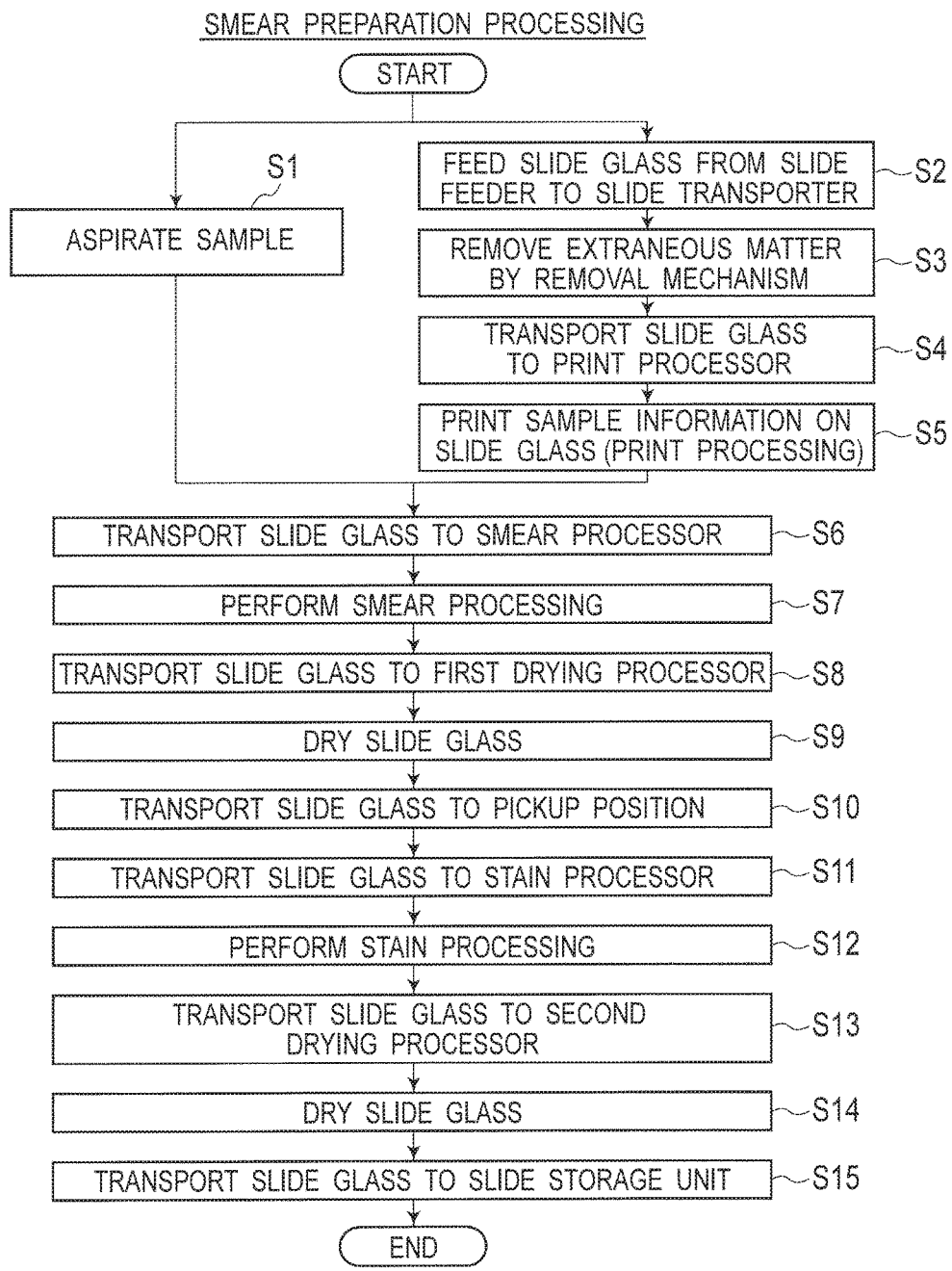
FIG. 15 is a flowchart illustrating smear preparation processing.

With reference to FIG. 15, description is given of an example of a smear preparation operation by smear preparation apparatus 300. Controller 230 controls smear preparation apparatus 300.

First, in Step S1 of FIG. 15, a sample is aspirated. Aspirator 220 aspirates the sample from sample container 211 transported to an aspiration position by sample transporter 210. In parallel with the processing in Step S1, slide glass 10 is fed to slide transporter 50 from slide feeder 20 in Step S2. To be more specific, slide transporter 50 locates slide holder mechanism 60 at feed height position 460 (see FIG. 11) at first feed position 401 or second feed position 402 (see FIG. 12). Slide feeder 20 passes slide glass 10 to slide holder mechanism 60. In Step S3, slide glass 10 held by slide transporter 50 is transported to removal position 403, and removal mechanism 120 performs processing of removing extraneous matter adhering to slide glass 10 held by slide transporter 50.

In Step S4, slide transporter 50 transports slide glass to print processor 30. Slide transporter 50 locates slide holder mechanism 60 at print height position 450 (see FIG. 9) at processing position 404 (see FIG. 12). In Step S5, print processor 30 performs print processing on slide glass 10 held by slide transporter 50.

In Step S6, slide transporter 50 transports slide glass 10 to smear processor 40. Slide transporter 50 locates slide glass 10 at smear height position 440 (see FIG. 7) at processing position 405 (see FIG. 12). In Step S7, smear processor 40 performs smear processing on slide glass 10 held by slide transporter 50.

In Step S8, slide glass 10 is transported to first drying processor 130. To be more specific, discharge mechanism 140 passes slide glass 10 to first drying processor 130 from slide transporter 50. In Step S9, first drying processor 130 performs drying processing on the sample smeared on slide glass 10.

In Step S10, transport mechanism 150 transports slide glass 10 to pickup position 410 (see FIG. 3). To be more specific, discharge mechanism 140 passes slide glass 10 to accommodation unit 151 in transport mechanism 150 from first drying processor 130. Transport mechanism 150 transports slide glass 10 set in accommodation unit 151 to pickup position 410.

In Step S11, slide glass 10 is transported to stain processor 160. To be more specific, transport mechanism 180 picks up slide glass 10 from transport mechanism 150 at pickup position 410, and transports slide glass 10 to stain processor 160. In Step S12, stain processor 160 performs stain processing on the sample smeared on slide glass 10.

In Step S13, slide glass 10 is transported to second drying processor 190. To be more specific, transport mechanism 180 passes slide glass 10 to second drying processor 190 from stain processor 160. In Step S14, second drying processor 190 performs drying processing on the sample smeared and stained on slide glass 10. Thus, a smear is prepared on slide glass 10.

In Step S15, slide glass 10 is transported to slide storage unit 200. To be more specific, transport mechanism 180 passes slide glass 10 to slide storage container 240 arranged in slide storage unit 200 from second drying processor 190. Thus, slide glass 10 with the smear prepared thereon is stored in slide storage unit 200. Then, the smear preparation processing is terminated.

One or more embodiments may be specified in the following paragraphs.

The transfer mechanism of the slide transporter may lift the slide holder mechanism after moving the slide holder mechanism to the slide feeder or the smear processor.

A sample smear method using a sample smear apparatus that feeds a slide glass before processing to a slide glass feed position and performs smear processing of the sample on the slide glass, comprising:
moving a slide holder mechanism to the slide glass feed position;
positioning the slide holder mechanism in a vertical direction by lifting the slide holder mechanism;
feeding the slide glass to the positioned slide holder mechanism;
moving the slide holder mechanism to a processing position for the smear processing after feeding the slide glass;
positioning the slide glass in the vertical direction by lifting the slide holder mechanism; and
performing the smear processing on the positioned slide glass.

According to one or more embodiments described above provide sample smear apparatus and sample smear method with simplify structures of a slide feeder and processors.

Note that the embodiment disclosed herein is to be considered in all respects as illustrative and not restrictive. The scope of the invention is indicated by the appended claims, rather than by the foregoing description of the embodiment, and all changes (modified examples) which come within the meaning and range of equivalency of the claims are therefore intended to be embraced therein.

The invention claimed is:

1. A sample smear apparatus comprising:
a slide feeder that feeds a slide glass before processing;
a smear processor that smears a sample on the slide glass;
a slide transporter including a slide holder mechanism with an upper surface to hold the slide glass and a transfer mechanism that moves the slide holder mechanism in a vertical direction and in a horizontal direction, the slide transporter arranged movably to the slide feeder and the smear processor, and
a print processor that performs printing on the slide glass, wherein
the smear processor comprises:
a drop unit that drops the sample on the slide glass on the slide holder mechanism; and
a smear member that comes into contact with the slide glass on the slide holder mechanism and smears the dropped sample on the slide glass on the slide holder mechanism,
the slide transporter is arranged movably to move the slide glass to: the slide feeder, the print processor, and the smear processor,
the print processor comprises a printer arranged at a position above the slide glass transported by the slide transporter, and
the printer is configured to come into contact with and perform printing on the slide glass on the slide holder mechanism.

2. The sample smear apparatus according to claim 1, further comprising a vertical positioning member provided in more than one of the slide feeder, the print processor, and the smear processor, that positions the slide holder mechanism or the slide glass in a vertical direction by coming into contact with a predetermined portion of the slide holder mechanism or the slide glass lifted by the transfer mechanism in the slide transporter.

3. The sample smear apparatus according to claim 2, wherein
the vertical positioning member includes a first positioning member provided in the smear processor, and
the first positioning member is arranged at a smear height position where to smear the sample on the slide glass, and locates a surface of the slide glass at the smear height position by coming into contact with the slide glass lifted by the transfer mechanism.

4. The sample smear apparatus according to claim 3, wherein
the first positioning member is arranged to come into contact with a corner of an upper surface of the slide glass lifted by the transfer mechanism.

5. The sample smear apparatus according to claim 4, wherein
the first positioning member is configured to come into contact with four corners of the upper surface of the slide glass lifted by the transfer mechanism.

6. The sample smear apparatus according to claim 2, wherein
the slide holder mechanism further includes a mount plate which forms an upper surface of the slide holder mechanism and a contact member which is positioned below the mount plate, and that serves as the predetermined portion to be lifted together with the mount plate by the transfer mechanism,
the vertical positioning member includes a second positioning member provided in the print processor, and
the second positioning member is positioned below the slide glass held on the mount plate, and locates the mount plate at a print height position of the slide glass by coming into contact with the contact member lifted by the transfer mechanism.

7. The sample smear apparatus according to claim 6, wherein
the contact member is made of resin, and is horizontally moved by the transfer mechanism during print processing while being kept in contact with the second positioning member.

8. The sample smear apparatus according to claim 6, wherein
the vertical positioning member further includes a third positioning member provided in the slide feeder, and
the third positioning member locates the mount plate at a feed height position of the slide glass by coming into contact with the contact member lifted by the transfer mechanism.

9. The sample smear apparatus according to claim 8, wherein
the second positioning member and the third positioning member are an integrally formed flat plate member, and the print height position and the feed height position are the same height position.

10. The sample smear apparatus according to claim 9, wherein
the flat plate member is positioned to cover a horizontal movable range of the transfer mechanism at a height position between the transfer mechanism and the slide holder mechanism, and includes a slit hole provided along a movement path of the slide holder mechanism, and
the transfer mechanism includes a column part that vertically passes through the slit hole to support the slide holder mechanism.

11. The sample smear apparatus according to claim 2, wherein
the slide holder mechanism further includes
a mount plate that forms an upper surface of the slide holder mechanism, and
a resilient elastic body that supports a lower surface of the mount plate.

12. The sample smear apparatus according to claim 11, wherein
the elastic bodies are provided at a predetermined interval along a longitudinal direction of the mount plate.

13. The sample smear apparatus according to claim 11, wherein
three or more of the elastic bodies are provided to surround the center of gravity of the mount plate, and each include a spring member which supports the lower surface of the mount plate.

14. The sample smear apparatus according to claim 1, wherein
the transfer mechanism moves the slide holder mechanism to the slide feeder so that the slide glass is fed onto the upper surface of the slide holder mechanism, and horizontally transfers the slide holder mechanism to the print processor and the smear processor in turn, and lift the slide glass held by the slide holder mechanism in the print processor and the smear processor to locate the slide glass to the respective height positions.

15. The sample smear apparatus according to claim 1, further comprising:
a removal mechanism that removes extraneous matter by emitting an air blast onto the surface of the slide glass held by the slide holder mechanism; and
an air pressure source which feeds an air pressure to the removal mechanism and the air cylinder.

16. The sample smear apparatus according to claim 1, wherein
the slide feeder includes:
a case part that holds slide glasses before processing in a stacked state; and
a discharger that feeds the slide glasses stacked in the case part, one by one, by pushing the slide glasses out from the case part.

17. A sample smear apparatus comprising:
a slide feeder that feeds a slide glass before processing;
a smear processor that smears a sample on the slide glass;
a slide transporter including a slide holder mechanism with an upper surface where to hold the slide glass and a transfer mechanism that moves the slide holder mechanism in a vertical direction and in a horizontal direction, the slide transporter arranged movably to the slide feeder and the smear processor, and
a print processor that performs printing on the slide glass, wherein
the smear processor comprises:
a drop unit that drops the sample on the slide glass on the slide holder mechanism; and
a smear member that comes into contact with the slide glass on the slide holder mechanism and smears the dropped sample on the slide glass on the slide holder mechanism,
the slide transporter is arranged movably to move the slide glass to: the slide feeder, the print processor, and the smear processor,
the print processor comprises a printer arranged at a position above the slide glass transported by the slide transporter,
the printer is configured to come into contact with and perform printing on the slide glass on the slide holder mechanism, and
the transfer mechanism includes an air cylinder that lifts up and down the slide holder mechanism in the vertical direction.

* * * * *